United States Patent [19]

Nashef et al.

[11] Patent Number: 5,215,541
[45] Date of Patent: Jun. 1, 1993

[54] SURFACTANT TREATMENT OF IMPLANTABLE BIOLOGICAL TISSUE TO INHIBIT CALCIFICATION

[75] Inventors: Aws S. Nashef, Costa Mesa; Ahmed I. Ahmed, Riverside, both of Calif.

[73] Assignee: Baxter International Inc., Deerfield, Ill.

[21] Appl. No.: 713,204

[22] Filed: Mar. 18, 1985

Related U.S. Application Data

[62] Division of Ser. No. 441,023, Nov. 12, 1982, abandoned.

[51] Int. Cl.$^5$ .............................................. A61L 27/00
[52] U.S. Cl. ........................................ 8/94.11; 623/1; 623/2; 623/3
[58] Field of Search ................... 8/94.11, 1; 3/1.4, 1.5; 424/333, 334; 623/1, 2, 3

[56] References Cited

U.S. PATENT DOCUMENTS

| | | | |
|---|---|---|---|
| 4,323,358 | 4/1982 | Lentz et al. | 8/94.11 |
| 4,383,832 | 5/1983 | Fraefel et al. | 8/94.11 |
| 4,402,697 | 9/1983 | Pollock et al. | 8/94.11 |
| 4,405,327 | 9/1983 | Pollock et al. | 8/94.11 |

OTHER PUBLICATIONS

Schwartz-Perry "Surface Active Agents . . . " pp. 9–10 Interscience, N.Y. (1949).
A. G. Marshall; *Biophysical Chemistry* (1978) pp. 148–172.
R. Harrison and G. Lunt; *Biological Membranes* (1975) p. 85.
C. F. Foxard, A. D. Keith; *Membrane Molecular Biology* (1972) pp. 38–40.

*Primary Examiner*—Prince Willis, Jr.
*Assistant Examiner*—John F. McNally
*Attorney, Agent, or Firm*—Debra D. Condino

[57] ABSTRACT

A process for the preparation of implantable biological tissue, and in particular bioprosthetic heart valves, which are prone to calcification after implantation. The process includes the treatment of tissue with an effective amount of a surfactant to reduce calcification of the implanted tissue.

12 Claims, No Drawings

SURFACTANT TREATMENT OF IMPLANTABLE BIOLOGICAL TISSUE TO INHIBIT CALCIFICATION

This application is a division, of application Ser. No. 441,023, filed Nov. 12, 1982, now abandoned.

BACKGROUND OF THE INVENTION

With the introduction of glutaraldehyde preservation of biological tissue, and in particular porcine bioprosthetic heart valves, it has become possible to: a) overcome the poor performance of early formaldehyde-preserved implanted tissue valves; b) discontinue the use of homograft valves; and c) avoid the undesirable use of anticoagulants required to prevent thromboembolism associated with the use of non-bioprosthetic (mechanical) heart valves, especially in children. Not unlike other similarly important discoveries, however it appears that the glutaraldehyde-preserved bioprosthesis has created its own dilemma.

Although the relatively biologically inert glutaraldehyde-preserved valves of Carpentier and others have demostrated excellent long-term durability in most instances, serious drawbacks such as tissue-fatigue and a propensity toward calcification have occured. Moreover, it was initially contemplated that children and adolescents would be among those deriving the greatest benefit from the glutaraldehyde-preserved bioprosthetic heart valves since the anticoagulants required with mechanical prosthesis could be eliminated. Results from an increasing number of recent clinical studies indicate that severe calcification of these tissues with relatively short-term failure is prevalent among children and adolescents. Thus, despite their long-term durability and overall reduced incidence of complications, these glutaraldehyde-preserved valves have been deemed by some to be unsuitable for use in children.

Calcification of tissue remains a mystery for the most part; however, it has previously been shown that various factors including calcium metabolism diseases, age, diet, degeneration of tissue components such as collagen, and turbulance are all involved to a certain extent. Recently, the occurrence of a specific calcium-binding amino acid (gamma carboxyglutamic acid), laid down after implantation of glutaraldehyde-preserved porcine xenografts, has been demonstrated; and it has been postulated to play a role in calcification. While calcification has been accompanied by degradative changes in the glutaraldehyde-treated collagen fibers of the implanted tissue, it remains unclear whether the dystrophic calcification is a cause or the result of tissue degeneration. Nevertheless, there has been a continued effort to elucidate the source of the calcification problem with implanted tissue.

In accordance with the present invention, we have developed a process which effectively reduces calcification of implanted biological tissue, and mantains the proper hemodynamic properties of the valve leaflets in bioprosthetic heart valves. This process advantageously reduces the tendency of bioprostheses toward calcification and overcomes some of the problems associated with the durability of xenograft heart valves.

SUMMARY OF THE INVENTION

In accordance with the present invention, disclosed is an improved process for treating biological tissue prior to implantation which results in a mitigation or reduction of calcification thereof after implantation. The process comprises contacting the biological tissue with a surfactant in an amount effective in reducing calcification of said tissue after implantation.

DETAILED DESCRIPTION OF THE INVENTION

In accordance with the present invention, it is contemplated that various types of implantable biological tissue derived from numerous animal sources and parts of the anatomy can be made resistant to calcification. Thus, the tissue can be derived from various sources such as but not limited to bovine, porcine, horse, sheep, kangaroo, or rabbit; and can include tendons, ligaments, heart valves, or tissue used to construct heart valves such as dura mater and pericardium. It is further contemplated that tissue used for augmentation such as skin patches, pericardial patches, aortic patches, and tympanic membranes is suitable in the present invention. In accordance with a preferred embodiment of the present invention, porcine heart valves or pericardial tissue which was fixed in glutaraldehyde and subsequently treated with a surfactant was implanted subcutaneously in rabbits. This treated tissue unexpectedly and beneficially effected a sustained mitigation or reduction of calcification after implantation. This sustained mitigation of calcification provides a method of increasing the durability of implanted tissue, particularly of heart valve bioprostheses.

In accordance with the present invention, the tissue may be stored and processed in conventional well-known conditions and may be fixed (tanned) conventionally in from about 0.2 to about 0.6 weight percent and preferably from about 0.5 to about 0.7 weight percent glutaraldehyde in either phosphate-buffered solutions, or phosphate-free buffers as described hereinafter. The tissue handling conditions as conventionally known are not considered part of out present invention unless otherwise stated. Likewise, tissue may be sterilized in 0.625 percent glutaraldehyde or from about 4 to about 5 percent formaldehyde.

Organic surfactants within the scope of the present invention include anionic, cationic, and nonionic surfactants and their salts. Preferred salts of the surfactants in the present invention include sodium, potassium, ammonium, and Halide. Anionic surfactants of the present invention are those having a relatively large hydrophobic region of hydrocarbon residues including both aliphatic groups, aromatic groups and combinations thereof bonded to a negatively charged ionic group. The aliphatic residues may be branched chains, straight chains, cyclic, heterocyclic, saturated or unsaturated. These hydrophobic residues may either be connected directly to an anionic group such as carboxylate, sulfate, or sulfonate; or connected thereto through an intermediate linkage such as an ester, amide, sulfonamide, ether, or aryl group. Anionic surfactants in one embodiment of the present invention are those having carboxylates bonded to the alkyl side chain of a steroid or through amino acids in the side chain; such as in the bile acids. Illustrative bile acids in accordance with the present invention include but are not limited to deoxycholic acid, cholic acid, lithocholic acid, taurocholic acid, and glycocholic acid, and their salts. A preferred bile acid and its salt which we have found effective in mitigation of calcification of implanted tissue is sodium deoxycholate. Anionic surfactants in accordance with the present invention further include those having a carboxylate group bonded to a straight-chained aliphatic group preferably having from about 8 to about 20 carbon atoms; such as the sodium salts of fatty acids. Anionic surfactants containing carboxylate groups in accordance with the present invention further include those having the carboxylate group coupled to a hydrophobic portion through an amide, sulfonamide, or ester linkage such as in the N-alkanoyl amino acids and N-acylated amino acids. Illustrative of N-alkanoyl amino acids are those including but not limited to surfactants having the formula $R_1CONR_2CHR_3CO_2-$ where $R_1$ is an aliphatic residue preferably having from about 8 to about 18 carbon atoms, $R_2$ is hydrogen or methyl, and $R_3$ is a conventional amino acid side chain. Illustrative side chains include the non-polar aliphatic side chains of alanine, leucine, isoleucine, valine, and proline; the aromatic rings of phenylalanine and tryptophan; the polar side chains of glycine, serine, threonine, cystine, and the like; and the charged polar groups of aspartic acid, glutamic acid, lysine, and the like. Preferred carboxlate containing surfactants in accordance with this embodiment of the present invention are those containing an amide linkage such as N-lauroylsarcosine.

Anionic surfactants in accordance with an alternate embodiment of the present invention include ethylene oxide modified sulfates of aliphatic alcohols, sulfated ethanol amides, or alkyl phenols such as the sulfonated alkylphenyl ethers. Further anionic surfactants include alkane sulfonic acids and alkylaryl sulfonic acids. Alkane sulfonic acids in accordance with the present invention include those having the sulfur directly attached to the hydrophobic residue, such as 1-decanesulfonic acid; or coupled through an ester, amide, or ether; such as N-methyltaurine. Alkylaryl sulfonates are those having the sulfur directly attached to an aromatic ring such as phenyl or napthyl which is, in turn, coupled to the hydrophobic residue preferably having from about 8 to about 18 carbon atoms. Illustrative of this latter type of surfactant is dodecylbenzenesulfonic acid.

Cationic surfactants in accordance with the present invention include alkyl quaternary amines and their halide salts. Preferably surfactants in the present invention include the chloride and bromide salts of tertiary amines connected directly to a hydrophobic residue or connected thereto through an amide linkage. Preferably the amines are directly connected to a relatively large hydrophobic portion having an aromatic residue such as benzene, pyridine or napthylene; aliphatic chain which is branched, unbranched, cyclic, saturated, or unsaturated; or a combination of both aromatic and aliphatic residues. Illustrative alkyl quaternary ammonium surfactants include but are not limited to cetylpyridinium chloride, cetyltrimethylammonium bromide, trimethylphenylammonium chloride, decyltrimethylammonium bromide, hexdecyltrimethylammonium bromide, and the like.

Nonionic surfactants in accordance with the present invention include polyoxyalkylene ethers, polyoxyalkylene alkylaryl ethers, aliphatic esters, polyethers, polyoxyalkylene ester derivatives, saccharide ester derivatives, and combinations thereof. Nonionic polyoxyalkylene, and preferably polyoxyethylene, ethers are those having a relatively long hydrophobic residue and a hydroxyl end connected by one or more alkylene oxide residues. Examples of polyoxyalkylene ethers are polyoxyethylene lauryl ether (Brij), polyoxyethylene oleyl ether, polyoxyethylene cetyl ether, and the like. Nonionic polyoxyalkylene, and preferably polyoxyethylene, alkylaryl ethers are those having a relatively large hydrophobic residue and a hydroxyl end connected thereto by an aryl, such as benzene or napthaline and one or more alkylene oxide residues. Examples of polyoxyalkylene alkylaryl ethers include polyethylene Glycol p-Isooctyl phenyl ethers such as Triton X-100 and the like. Nonionic polyethers are those having the formula $CH_3(CH_2)_N-O-(C_2H_4O)_M$ where N is about 11, and M is about 23.

Nonionic aliphatic esters include aliphatic fatty acid esters, polypropyleneglycol fatty acid esters such as propyleneglycol monostearate, and glycerol fatty acid esters such as glycerol monostearate. Aliphatic fatty acid esters are those having the formula $R_4COOR_5$ where $R_4$ is an alkyl preferably having from about 8 to about 20 carbon atoms, and $R_5$ is an aliphatic residue having from 1 to about 5 carbon atoms. Saccharide and polyoxyalkylene ester derivatives are those having either a 5 or 6 carbon sugar in the former or a polyoxyalkylene chain in the latter coupled to a relatively long hydrophobic residue through an ester bond. Illustrative saccharide derivatives include sorbitol coupled to fatty acids to form surfactants such as sorbitan trioleate, sorbitan strearate, sorbitan monooleate, and the like. Polyoxyalkylene ester derivatives include polyoxyethylene monooleate, polyoxyethylene monostearate, and the like. Combinations of polyoxyalkylene ether derivatives and sorbitol ester derivatives found to be useful in the present invention include polyoxyethylene sorbitan fatty acid derivatives such as polyoxyethylene (20) sorbitan monooleate (Polysorbate-80, Tween-80 manufactured by DIFCO).

In accordance with the present invention, the effective concentration of surfactant will vary somewhat depending on the molecular weight thereof; and is preferably from about 0.1 to about 10 percent (w/v) and more preferably from about 0.5 to about 5 percent. Most preferably, the surfactant concentration is from about 0.5 to about 1.5 percent. Moreover, the treatment of the tissue with surfactant can be performed during the fixation (tanning) process, during the sterilization process, or in a separate step after fixation and prior to sterilization; and from about 2 to about 30 hours and preferably from about 6 to about 24 hours.

In accordance with a preferred embodiment of the present invention, the tissue is treated with surfactant at temperatures of from about 20° C. to about 40° C. In one embodiment, the surfactant is included in the sterilization step whose effectiveness has been found to be enhanced at temperatures above room temperature (20° C.) to a range of from about 30° to 40° C.

In accordance with the present invention, it is preferable to store, fix, and sterilize the tissue within a tissue-stabilizing pH range; that is, within a pH range that is not deleterious to the tissue components. A preferred pH range is from about 7.0 to about 7.6, and a more preferred pH range is from about 7.1 to about 7.4. The most preferred pH in accordance with the present invention is 7.3.

Buffers used in accordance with one embodiment of the present invention are preferably stable, non-interacting with the stabilization process, and have a buffering capacity sufficient to maintain an acceptable pH, particularly during the fixation of the tissue. The choice of the appropriate buffer, and its concentration will depend upon specific tissue preparation conditions; variations of which have been introduced by several manufacturers. The buffers can be either conventional 0.01–0.02M phosphate-buffered saline (PBS) or phosphate-deficient solutions such as those containing less phosphate than these 0.01 to 0.02M PBS solutions, and preferably less than about 0.001 to about 0.002M phosphate. Preferred buffers in accordance with the present invention include borate, carbonate, bicarbonate, cacodylate (found to be nontoxic in animals), and other synthetic, artificial, or organic buffers such as HEPES, N-2-hydroxyethylpiperazine-N'-2-ethanesulphonic acid; MOPS, 2-(N-morpholino) propane-sulfonic acid; and PIPES, 1,4-piperazinediethanesulphonic acid.

Preferably, the buffered or unbuffered solutions, used in accordance with the present invention should not interfere with the tissue stabilizing process afforded by fixing agents such as glutaraldehyde. That is, they should not react with the fixing agent or prevent the fixing agent from achieving proper fixation of the tissue. Illustrative of this are buffers containing primary and secondary amines such as tris(hydroxymethyl)aminomethane (Tris), which are known to react with the aldehyde groups of glutaraldehyde or formaldehyde and thus interfere with the normal tissue stabilization process.

The present invention is further illustrated by the following examples which are not intended to be limiting:

EXAMPLE I

Extracted porcine aortic heart valve tissue was throroughly rinsed and shipped in an isotonic (285±15 milliosmols) solution of 0.02M phosphate-buffered saline (0.885 weight percent sodium chloride) at pH 7.3 and at about 4° C.; and fixed in 0.625 weight percent glutaraldehyde in an isotonic phosphate-buffered solution at pH 7.4 and at room temperature.

EXAMPLE II

Extracted porcine aortic heart valve tissue was thoroughly rinsed and shipped in an isotonic (285±15 milliosmols) solution containing 0.54 grams/liter of the sodium salt of N-2-hydroxyethylpiperazine-N-2-ethanesulphonic acid (HEPES) and 0.885 weight percent sodium chloride at pH 7.3 at about 4° C.; and fixed with 0.625 weight percent glutaraldehyde in an isotonic solution containing 5.39 grams/liter of the sodium salt of HEPES (0.02M), 0.440 weight percent sodium chloride and 2.6 grams/liter of $MgCl_2.6H_2O$ at room temperature.

EXAMPLE III the extracted tissue of Example I was further sterilized in a 0.02M phosphate-buffered saline (0.885 weight percent sodium chloride) solution (3 square inches of tissue in 70 ml) containing 4±0.4 percent sorbitan monooleate polyoxyethylene (Tween-80), pH 7.3 at 35° C. The tissue was removed from the solution after 24 hours, rinsed 4 times with 0.625 percent glutaraldehyde in 0.02M phosphate-buffered saline for 10 minutes each and implanted subcutaneously in growing rabbits. The value tissue was retrieved up to six weeks later at regular one-week intervals. After retrieval, the extent of tissue calcification was assessed by quantitatively monitoring the weight percent calcium in dried tissue using atomic absorption analysis; and histologically by visually monitoring the degree of calcification in Von Kossa-stained tissue sections. Both the histologic and quantitative results indicate that the implanted valve tissue effected a significant reduction in calcification compared to a valve tissue treated identically to that described herein in all essential details with the exception that no Tween-80 was added.

EXAMPLE IV

The extracted tissue of Example II was further sterilized in a 0.02M HEPES (5.39 gram/liter of the sodium salt) buffered saline solution (3 square inches of tissue in 70 ml) containing 4±0.4 percent formaldehyde, 22.5 percent ethanol, 0.26 grams/liter $MgCl_2.6H_2O$, at pH 7.3 and 35° C. The tissue was removed from the solution after 24 hours, rinsed 4 times with 0.625 percent glutaraldehyde in 0.02M HEPES-buffered saline for 10 minutes each, and implanted subcutaneously in growing rabbits. The valve tissue was retrieved up to six weeks later at regular one-week intervals. After retrieval, the extent of tissue calcification was assessed by quantitatively monitoring the weight percent calcium in dried tissue using atomic absorption analysis; and histologically by visually monitoring the degree of calcification in Von Kossa-stained tissue sections. The results of the histologic and quantitative analyses were used for comparison with results obtained for tissue treated with various surfactants.

EXAMPLE V

The extracted tissue of Example II was further sterilized in a 0.02M HEPES (5.39 gram/liter of the sodium salt) buffered saline solution (3 square inches if tissue in 70 ml) containing 4±0.4 percent formaldehyde, 22.5 percent ethanol, 11.3 mM (1.5 weight percent) sorbitan monooleate polyoxyethylene (Tween-80), 0.26 grams/liter $MgCl_2.6H_2O$, at pH 7.3 and 35° C. The tissue was removed from the solution after 24 hours, rinsed 4 times with 0.625 percent glutaraldehyde in 0.02M HEPES-buffered saline for 10 minutes each, and implanted subcutaneously in growing rabbits. The valve tissue was retrieved up to six weeks later at regular one-week intervals. After retrieval, the extent of tissue calcification was assessed by quantitatively monitoring the weight percent calcium in dried tissue using atomic absorption analysis; and histologically by visually monitoring the degree of calcification in Von Kossa-stained tissue sections. Both the histologic and quantative results indicate that the implanted valve tissue effected a significant reduction in calcification compared to the valve tissue treated in accordance with Example IV which did not include surfactant.

EXAMPLE VI

The extracted tissue of Example II was treated identically to that of Example V in all essential details with the exception that no ethanol was added. After sterilization and rinsing the tissue was implanted in growing rabbits and retrieved up to six weeks later at regular one-week intervals. After retrieval, the extent of tissue calcification was assessed by quantitatively monitoring the weight percent calcium in dried tissue using atomic absorption analysis; and histologically by visually monitoring the degree of calcification in Von Kossa-stained tissue sections. Both the histologic and quantitative results indicate that there was no effect of the presence of ethanol in the surfactant solution on mitigating calcification.

EXAMPLE VII

The extracted tissue of Example II was treated, implanted in growing rabbits, and analyzed identically to that of Example V in all essential details with the exception that 24.0 mM Triton X-100 (1.5 weight percent) was used in place of Tween-80. The results indicate that the implanted valve tissue effected a significant reduction in calcification compared to the valve tissue treated in accordance with Example IV which did not include surfactant.

EXAMPLE VIII

The extracted tissue of Example II was treated, implanted in growing rabbits, and analyzed identically to that of Example V in all essential details with the exception that 57.2 mM 1-decanesulfonic acid (1.5 weight percent) was used in place of Tween-80. The results indicate that the implanted valve tissue effected a significant reduction in calcification compared to the valve tissue treated in accordance with Example IV which did not include surfactant.

EXAMPLE IX

The extracted tissue of Example II was treated, implanted in growing rabbits, and analyzed identically to that of Example V in all essential details with the exception that 45.9 mM dodecylbenzenesulfonic acid (1.5 weight percent) was used in place of Tween-80. The results indicate that the implanted valve tissue effected a significant reduction in calcification compared to the valve tissue treated in accordance with Example IV which did not include surfactant.

EXAMPLE X

The extracted tissue of Example II was treated, implanted in growing rabbits, and analyzed identically to that of Example V in all essential details with the exception that 42 mM potassium coconut fatty acid hydrolyzed protein (Maypon-4C) (1.5 weight percent) was used in place of Tween-80. The results indicate that the implanted valve tissue effected a significant reduction in calcification compared to the valve tissue treated in accordance with Example IV which did not include surfactant.

EXAMPLE XI

The extracted tissue of Example II was treated, implanted in growing rabbits, and analyzed identically to that of Example V in all essential details with the exception that 55.3 mM N-lauroylsarcosine (1.5 weight percent) was used in place of Tween-80. The results indicate that the implanted valve tissue effected a significant reduction in calcification compared to the valve tissue treated in accordance with Example IV which did not include surfactant.

EXAMPLE XII

The extracted tissue of Example II was treated, implanted in growing rabbits, and analyzed identically to that of Example V in all essential details with the exception that 36.2 mM deoxycholic acid (1.5 weight percent) was used in place of Tween-80. The results indicate that the implanted valve tissue effected a significant reduction in calcification compared to the valve tissue treated in accordance with Example IV which did not include surfactant.

EXAMPLE XIII

The extracted tissue of Example II was treated, implanted in growing rabbits, and analyzed identically to that of Example V in all essential details with the exception that 53.5 mM decyltrimethylammonium bromide (1.5 weight percent) was used in place of Tween-80. The results indicate that the implanted valve tissue effected a significant reduction in calcification compared to the valve tissue treated in accordance with Example IV which did not include surfactant.

EXAMPLE XIV

The extracted tissue of Example II was treated, implanted in growing rabbits, and analyzed identically to that of Example V in all essential details with the exception that 41.2 hexadecyltrimethylammonium bromide (1.5 weight percent) was used in place of Tween-80. The results indicate that the implanted valve tissue effected a significant reduction in calcification compared to the valve tissue treated in accordance with Example IV which did not include surfactant.

EXAMPLE XV

The extracted tissue of Example II was treated, implanted in growing rabbits, and analyzed identically to that of Example V in all essential details with the exception that 87.4 trimethylphenylammonium chloride (1.5 weight percent) was used in place of Tween-80. The results indicate that the implanted valve tissue effected a significant reduction in calcification compared to the valve tissue treated in accordance with Example IV which did not include surfactant.

EXAMPLE XVI

The tissue treated in accordance with the process of Example III was further analyzed to assess the integrity of the tissue after exposure to surfactant. The results of our analysis show that there was no significant difference in the cross-link stability as indicated by shrinkage temperature, tissue stability as indicated by pronase digestion; amino acid analysis, ninhydrin analysis; uronic acid content, histologic examination as indicated by staining with Hematoxylin Eosin, aldehyde fuschin, PAS/alcian blue, and Trichrome; and surface morphology as determined by scanning electron microscopy and transmission electron microscopy.

The present invention has been described in specific detail and in reference to its preferred embodiments; however, it is to be understood by those skilled in the art that modifications and changes can be made thereto without departing from the spirit and scope thereof.

We claim:

1. A method for reducing calcification of biological tissue after implantation in an animal comprising:
   fixing the biological tissue under tissue fixing conditions; and
   contacting the biological tissue with a solution of an anionic surfactant prior to implantation in an amount effective in reducing calcification of the tissue after implantation; wherein the surfactant is selected from the group consisting of ethylene oxide sulfates of aliphatic alcohols, sulfates of alkylphenols, alkane sulfonic acids, alkylaryl sulfonic acids, salts of bile acids, salts of fatty acids, N-alkanoyl amino acids, N-acylated amino acids, sulfated ethanol amides, sulfated alkylphenol ethers, and salts thereof.

2. The process of claim 1 wherein the surfactant is the sodium, potassium or ammonium salt.

3. The process of claim 1 wherein the tissue is contacted with the surfactant during fixation.

4. The process of claim 1 wherein the tissue is contacted with the surfactant during post-fixation sterilization.

5. The process of claim 1 wherein the amount of surfactant in the solution is from about 0.1 to about 10 weight percent.

6. The process of claim 5 wherein the tissue is contacted with the surfactant solution for a time from about 2 to about 30 hours.

7. The process of claim 1 wherein the amount of surfactant in the solution is from 0.5 to about 5 weight percent.

8. The process of claim 1 wherein the tissue is fixed with glutaraldehyde.

9. The process of claim 1 wherein the tissue is fixed with glutaraldehyde; and is contacted with a solution having from about 0.1 to about 10 weight percent of surfactant selected from the group consisting of ethylene oxide sulfates of aliphatic alcohols, sulfates of alkylphenols, alkane sulfonic acids and alkylaryl sulfonic acids.

10. The process of claim 1 wherein the biological tissue is tendon, ligament, heart valve, dura mater, or pericardium.

11. The process of claim 1 wherein the amount of surfactant in the solution is from about 0.1 to about 1.5 weight percent; the biological tissue is tendon, ligament, heart valve, dura mater, or pericardium, and is fixed with glutaraldehyde; the surfactant is N-lauroylsarcosine; and the tissue is contacted with the surfactant solution for a time from about 6 to about 24 hours at a pH of from about 7.0 to about 7.6.

12. The process of claim 1 wherein the tissue is contacted with surfactant during post-fixation sterilization and the surfactant solution further comprises from about 4 to about 5 percent formaldehyde.

* * * * *